United States Patent
Goller et al.

(10) Patent No.: US 7,202,081 B2
(45) Date of Patent: Apr. 10, 2007

(54) SIMULTANEOUS DETERMINATION OF CELL PROLIFERATION INHIBITION ACTIVITY AND TOXICITY

(75) Inventors: Bernhard Goller, Penzberg (DE); Manfred Kubbies, Penzberg (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 425 days.

(21) Appl. No.: 10/776,733

(22) Filed: Feb. 11, 2004

(65) Prior Publication Data

US 2004/0180390 A1    Sep. 16, 2004

(30) Foreign Application Priority Data

Mar. 12, 2003  (EP) ................... 03005335

(51) Int. Cl.
*C12N 5/00* (2006.01)
(52) U.S. Cl. ...................................... 435/325
(58) Field of Classification Search ............ None
See application file for complete search history.

(56) References Cited

OTHER PUBLICATIONS

Ferlini et al. Pharmacology & Toxicology 2001, 89, 231-236.*

\* cited by examiner

*Primary Examiner*—Ralph Gitomer
*Assistant Examiner*—Bin Shen
(74) *Attorney, Agent, or Firm*—George W. Johnston; Patricia S. Rocha-Tramaloni (57) ABSTRACT

A method for the simultaneous determination of cell proliferation inhibition activity and cell toxicity (induction of cell death) of a substance using a proliferating mammalian cell sample as a test system.

5 Claims, 6 Drawing Sheets

Fig. 2 – Part 1: CD34 cell count and cytotoxicity analysis by FACS

Fig. 2 – Part 2: CD34 cell count and cytotoxicity analysis by FACS

Fig. 2 – Part 3: CD34 cell count and cytotoxicity analysis by FACS

Fig. 2 – Part 4: CD34 cell count and cytotoxicity analysis by FACS

Fig. 3

SIMULTANEOUS DETERMINATION OF CELL PROLIFERATION INHIBITION ACTIVITY AND TOXICITY

FIELD OF THE INVENTION

The invention provides a method for the simultaneous determination of cell proliferation inhibition activity and toxicity of a substance which can be performed within the screening of such a substance for its activity in proliferation inhibition.

BACKGROUND OF THE INVENTION

The identification of substances which are potent proliferation inhibitors is of great importance during drug discovery, preferably in the field of oncology. There exists a variety of in vitro cell-based assays for the investigation of the antiproliferative effect of such candidate substances. Examples of such assays are, for instance, the MTT colorimetric assay, the [3H] thymidine uptake assay, and the WST assay (Johnston, P., in: Cellular Assays in HTS, Methods in Molecular Biology, Vol. 110, Janzen W. P. (ed.), Humana Press, NJ, pp. 107–116; Bellamy, W. T., Drugs 44 (1992) 690–708). In regard to drug development, it is preferable that such assays can be used in high throughput screening of large numbers of potential drug candidates.

For the determination of the proliferation status of hematopoietic cells, it is known to contact the cell population with the substance to be investigated ("test substance") and a reagent capable of generating luminescence in the presence of ATP and detecting the luminescence as a measure of the proliferation status (US 2002/0146680). An assay for determining the number of cells in cell culture by fluorescence measurement is described in U.S. Pat. No. 5,972,639.

The above-described assays are time-consuming, provide only limited results, and do not discriminate between inhibition of proliferation and induction of cell death. Therefore, there exists a need for an assay that is simple to perform and allows the determination of the influence of a test substance on both cell proliferation and the induction of cell death simultaneously. Moreover, it would be preferable for such assay to be automated.

SUMMARY OF THE INVENTION

The invention provides a method for the simultaneous determination of cell proliferation inhibition activity and cell toxicity (induction of cell death) of a substance using a proliferating mammalian cell sample as a test system, characterized by a) treating said cell sample which is present in a predetermined amount (e.g. volume) with said substance in at least two different predetermined concentrations;

b) treating said cell sample with a first fluorescence dye staining specifically either dead cells or viable cells and optionally with a second fluorescence dye staining all cells;

c) adding to said cell sample a predetermined amount of latex particles with a size ranging from about 1 to about 20 µm to said volume and optionally staining said latex particles with a third fluorescence dye;

d) determining the ratio of the amount of total cells to the amount of latex particles in said sample;

e) determining with the results of step d) and by flow cytometric analysis in said sample the number of dead cells or viable cells by fluorescence light emitted by said first fluorescence dye at a first wavelength;

the number of total cells per volume by scatter light at a first angle or alternatively by fluorescence light emitted by said second fluorescence dye at a second wavelength;

the number of latex particles per volume by scatter light at a second angle or alternatively by fluorescence light emitted by said third fluorescence dye at a third wavelength;

f) and determining with the results of step d) and e) cell proliferation activity and toxicity of said substance.

In an embodiment of the invention, the cell sample is present as a cell suspension or as adherent cells.

In a preferred embodiment of the invention, the dead cells are specifically stained by a fluorescence dye and the number of latex particles and cells is measured by differential side scatter light and forward scatter light.

In a further preferred embodiment of the invention, the cells are human $CD34^+$ progenitor cells.

In a preferred embodiment of the invention, the method is performed in at least five different concentrations of said substance to be investigated (test substance), which preferably enables the calculation of $IC_{50}$ values for proliferation and induction of cell death. Preferably, the concentration range is of a factor of about 1 to 10,000.

After treating the cells with the test substance, the cells are cultivated under standard conditions that would allow cell proliferation. In a preferred embodiment of the invention, the cells are cultivated in parallel in multiple devices, preferably in multi-well microtiter plates. In addition, also the test substances are added to these devices in the different concentrations, preferably by an automatic pipetting means.

DETAILED DESCRIPTION OF THE INVENTION

Delayed cell growth during cultivation of cells in the presence of a test substance suspected to be a cell inhibitor can be caused by cell death and/or by cell proliferation inhibition. Therefore, from a mere determination of the amount of cells after cultivation with a test substance it is not possible to conclude directly the toxicity and/or inhibition activity of the substance. It is necessary to know the amounts of viable and dead cells and their ratio in regard to the total cell amount to be able to make such a determination. The invention provides a method for simultaneous determination of these parameters in a rapid manner. In addition, the method according to the invention can be automated and therefore allows for high throughput investigation of toxicity and proliferation inhibition activity of test substances.

Figure 3:
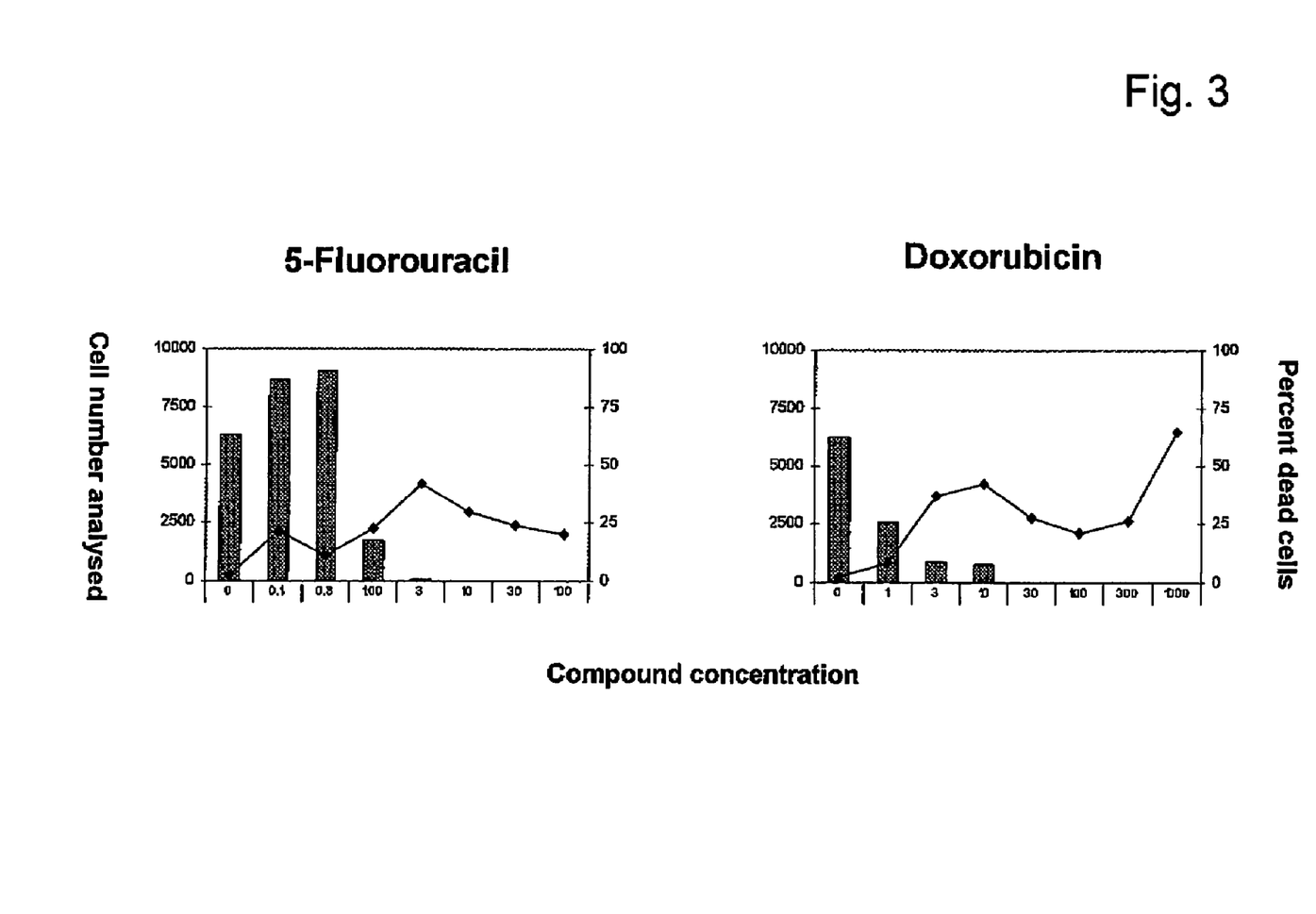
FIG. 3 Cell number and percentage of dead cells quantitated from a FACS analysis as shown in FIG. 2. Two typical cytotoxic compounds, 5-fluorouracil (0.1–100 µmol/l) and doxorubicine (1–1000 ng/ml), are displayed. The $IC_{50}$ value for the cell number analysis corresponds to 0.34 µmol/l and 0.67 µg/ml for 5-fluorouracil and doxorubicine, respectively.

According to the invention, a defined (predetermined) aliquot of latex particles is added to each cell cultivation device. Based on the counting of the latex particles during flow cytometric analysis, the volume of the liquid in which all the counting were performed can be estimated. Therefore, the invention provides a method for simultaneous determination of the amount of total cells per volume (which is a measure of cell proliferation) and the amount of viable cells per volume after cultivation in the presence of a test substance suspected to be a proliferation inhibitor and/or to be toxic to the cells of the test system. The comparison of the amount of total cells with the amount of dead cells or viable cells for different concentrations of the substance provides the information on the relation between inhibition of cell proliferation and toxicity of the substance. This can be deduced immediately from FIG. 3. If the percentage of dead cells to total cells increases significantly whereas the number of total cells decreases, this indicates high toxicity of the test substance. If, however, the percentage of dead cells to total cells does not increase significantly with increasing test substance concentration whereas the number of total cells decreases, then the substance shows a low toxicity. Examples of substances with high toxicities are shown in FIG. 3. 5-fluorouracil and doxorubicine are substances which display toxicity in parallel to significant proliferation inhibition. For 5-fluorouracil the percentage of dead cells to total cells is in the range between 0 and 25% for the concentration range of the substance in which proliferation inhibition is found as more than 50%. For doxorubicine the percentage of dead cells increases with substance concentration up to 40% and even higher whereas proliferation inhibition is about 80%.

The cultivation process of the proliferating cells, e.g. CD34 cells, is performed as described below. Prior to FACS analysis, the fluorescence dye for staining the viable or dead cells and a distinct number of latex beads are added to each well device (preferably microtiter plates, or the like) for staining of viable or dead cells and counting of latex particles as a measure of cell culture medium volume analyzed, respectively. After adding the substances to be investigated and after performing the cell cultivation in the different devices, the microtiter plate is placed onto an automated pipetting instrument which routes aliquots of the cell sample from each well through the FACS (Fluorescence Activated Cell Sorter) flow chamber. A distinct number of latex beads is being analyzed (thereby giving information about the medium volume measured), measurement is stopped and the pipetting robot takes aliquots from the next well, and analysis starts again as before.

The term "substances to be investigated" or "substances" or "test substances" as used herein describes any substance which is being assessed as to whether it has, or is suspected of having, proliferation inhibition or cytotoxic activity on certain cells. Said substances can be, for example, antibodies, polypeptides, short peptides, oligonucleotides, or low molecular weight chemical compounds. The test substances are used in at least two different concentrations, preferably, however, in more concentrations, for example five different concentrations or more. The reasons for this is that based on the results for such different concentrations, it is possible to investigate the concentration dependent proliferation inhibition and cell death induction very easily and decide whether the substance inducts cell death considerably and/or inhibits proliferation. For the comparison of these values, especially for the comparison of the concentration dependence of proliferation and induction of cell death, it is possible to identify test substances that show for example strong proliferation inhibition without considerable induction of cell death. In addition, performing the method of the invention at different concentrations allows calculation of $IC_{50}$ values both for proliferation ("proliferation activity") and induction of cell death ("toxicity"). The concentrations and the range of concentrations depend on the potency of the test substance and also on the type of cell used for the investigation. Usually, the concentration range is in the micromolar range, typically between about 0.01 μM/ml and 100 μM/ml.

The term "cell" as used herein describes proliferating mammalian cells that are useful as a test system for performing proliferation assays. Such cells are well-known in the art and include, for example, human $CD34^+$ progenitor and stem cells, lymphocytes, normal fibroblasts/keratinocytes, normal endothelial- and epithelial cells, artificial transformed mammalian cells, leukemic cells and solid tumor cells. The proliferation of such cells can be inhibited by known inhibitors such as paclitaxel, doxorubicine or 5-fluorouracil.

Usually, the cells are seeded in parallel devices and propagated in suspension. Usually, and, for example, if 96 well microtiter plates are used for the cultivation of CD34 cells, 100 to 400 cells/200 μl are seeded per well and propagated preferably until they have reached about 10,000 cells/200 μl per well under standard conditions (without substance to be investigated). For cultivation of the cells, conventional cultivation media, preferably with added growth factors, are used.

The term "latex particles" as used herein describes such latex particles as are widely used in calibrating fluids for automated instruments for cell counting. Such latex particles are described, for example, in U.S. Pat. No. 3,977,995. Such latex particles usually consist of a synthetic latex made from polystyrene polyvinyl toluene or styrene divinylbenzene copolymer. The particle size usually ranges from 1 to about 20 μm and the particles are added to the cell suspension in an amount of about 10,000 particles/200 μl.

The measurement of the parameters for the determination according to the invention is performed by flow cytometric analysis in an apparatus wherein fluorescence at different wavelengths and scatter light at different angles can be measured and correlated with the amount of cells providing such signals. The parameters are determined while the cells from one sample are flowing through the analytical means of the apparatus either in parallel or immediately one parameter after another (simultaneous determination). Preferably, such a determination is performed by the use of an analytical FACS instrument. Scatter light is measured at different angles, preferably as forward scatter light (FSC) (maximum scatter light angle up to 20°, preferably lower) and side scatter light (SSC) (angle about 90°). Though cells and latex particles might not differ considerably in their size, their behavior in relation to light scatter is considerably different, presumably based on the internal structure and shape of the cells as well as on their different refractory index. Based on this difference, the cells (viable/proliferating, viable arrested cells and dead cells) can be easily discriminated from the latex particles by a considerably different scatter light angle. SSC refers to the latex beads and FSC refers to cells (cf. FIG. 2a). However, it is also possible to stain all cells or all latex particles with fluorescence dyes and discriminate latex particles and cells by the investigation of fluorescence light at different wavelengths. The use of the parameters measured depends simply on the possibilities and convenience provided by the apparatus used. If an apparatus is able to measure fluorescence light simultaneously at three or four different fluorescence wavelengths, latex particles, all cells and either the dividing or dead cells can be labeled specifically with fluorescence dyes. Therefore, all combinations of scatter light and fluorescence light can be used for the measurement of the parameters with the provision that the scatter light parameter is not useful for a direct discrimination of latex particles and dead cells of viable and proliferating and of viable and arrested cells.

The term "fluorescence dye staining specifically dead cells or viable cells" as used herein describes dyes which enter only dead cells (e.g. propidium iodide), or which enrich only in viable cells (e. g. fluoresceindiacetate). If cell counting of all cells is required, fluorescent dyes are useful for staining dead cells as well as for staining viable cells (e.g. Hoechst 33342). Numerous fluorescence dyes useful for selective labeling of viable or dead cells are described (e.g. catalog from Molecular Probes; [online], Retrieved from the Internet: RL:www.molecularprobes.com/>. The fluorescence dyes are added in an appropriate amount, which is, for example, about 1 µg/ml final concentration.

In one embodiment, the invention provides a method for the simultaneous determination of cell proliferation inhibition activity and cell toxicity (induction of cell death) of a substance using a proliferating mammalian cell sample as a test system, characterized by a) treating said cell sample, which preferably is present as a cell suspension or as adherent cells, and which is present in a predetermined amount (e.g. volume) with said substance in at least two different predetermined concentrations;

b) treating said cell sample with a first fluorescence dye staining specifically either dead cells or viable cells and optionally with a second fluorescence dye staining all cells;

c) adding to said cell sample a predetermined amount of latex particles with a size ranging from about 1 to about 20 µm to said volume and optionally staining said latex particles with a third fluorescence dye;

d) determining the ratio of the amount of total cells to the amount of latex particles in said sample;

e) determining with the results of step d) and by flow cytometric analysis in said sample the number of dead cells or viable cells by fluorescence light emitted by said first fluorescence dye at a first wavelength;

the number of total cells per volume by scatter light at a first angle or alternatively by fluorescence light emitted by said second fluorescence dye at a second wavelength;

the number of latex particles per volume by scatter light at a second angle or alternatively by fluorescence light emitted by said third fluorescence dye at a third wavelength;

f) and determining with the results of step d) and e) cell proliferation activity and toxicity of said substance.

The following examples are provided to aid the understanding of the present invention, the true scope of which is set forth in the appended claims. It is understood that modifications can be made in the procedures set forth without departing from the spirit of the invention.

EXAMPLE

Human cord blood CD34+ cells were isolated to high purity (>90%) by immunomagnetic cell sorting, aliquoted and frozen in DMSO containing medium. For cell culture setup, frozen CD34+ cells were thawed and 200 cells were seeded in 200 µl complete medium of a well of a 96 well plate. The basal cell culture medium consisted of IMDM-Medium supplemented with 20% human AB serum and antibiotics (pen/strep). The CD34+ cells were activated by addition of following cytokine cocktail: hu-SCF (100 ng/ml), hu-IL6 (10 ng/ml), hu-GM-CSF (100 U/ml), hu-TPO (25 ng/ml) and hu-EPO (5 U/ml). Cultivation was performed in incubators at 37° C., high humidity and 7% $CO_2$.

Two different experimental setup were used: 1) addition of the inhibitor compound prior supplementation of the medium with cytokines to hit preferentially resting cells, and 2) addition of inhibitor compound 4 days after CD34 activation with cytokines to hit preferentially activated cells.

Figure 1:
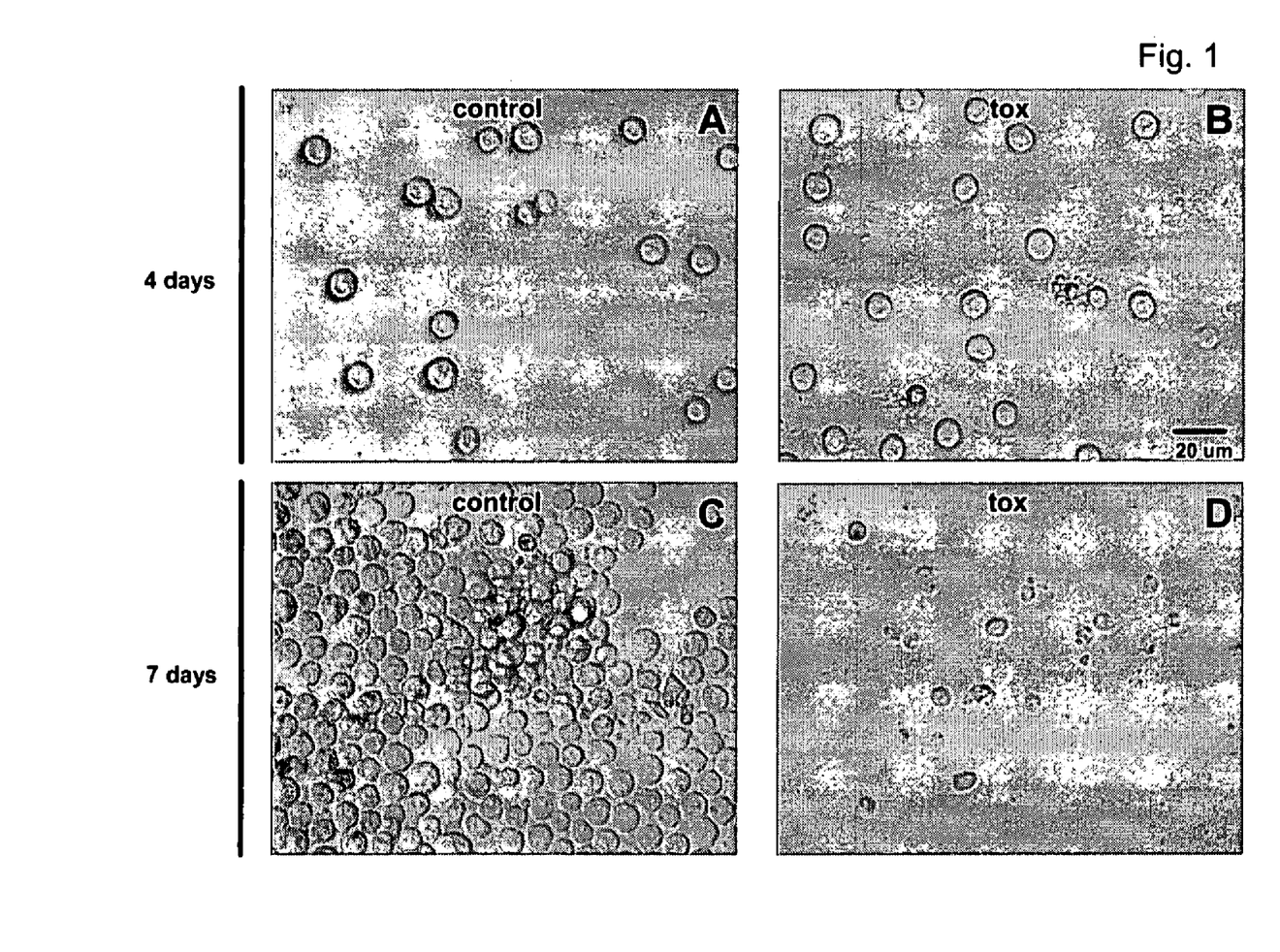
FIG. 1 Microscopic analysis of cell growth and cell death in CD34 cell populations. Cytokine stimulated CD34 cell were cultivated for 4 and 7 days untreated or treated with a cytotoxic compound.

As shown in FIG. 1, activated and viable CD34 cells appear as large, spheroid cells after 4 day cultivation period (panelA). The cell number increased significantly when the cells were grown for additional 3 days (panel C). A cytotoxic drug induced cell death in CD34 cells which appear fragmented in microscopic images after a 4 day culture period (panel B), and the number of fragmented cells increased without any significant increase of the cell number (panel D).

Dependent on the proliferation rate of the CD34+ cells, harvest and analysis of cell number and cytotoxicity was performed after 9–10 d cell culture. The cell number and cytotoxicity was analysed by FACS technique. The number of cells present in the well was counted by comparison with an internal bead standard. A aliquot of 10000 beads was added to each well harboring 200 µl medium volume FLUO-SPHERES® polystyrene, 15 µm; Molecular Probes).

Figure 2:
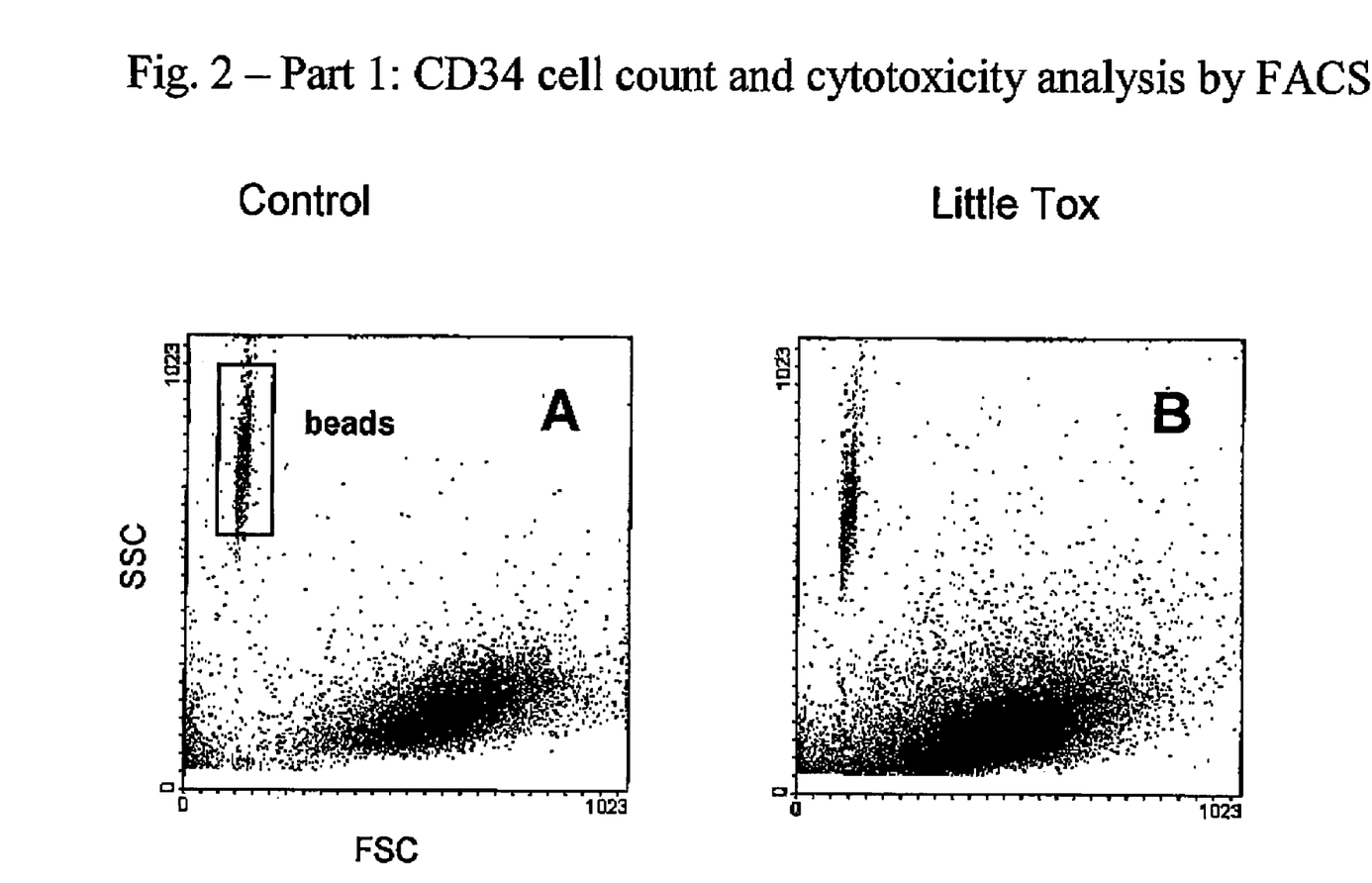
FIG. 2 FACS analysis of standard beads, and viable and dead cytokine stimulated CD34 cells cultivated for 10 days. Cell were either untreated (left row) or treated with cytotoxic compound inducing different levels of cytotoxicity.

As displayed in FIG. 2, in a typical FACS instrument setting, the viable cells appear in the middle/right position of the forward scatter (FSC) and low side scatter (SSC) but the standard beads added are present in a region with lower FSC and high SSC (panel A). A gate, shown as rectangular region, was set onto the standard beads, a distinct number was counted, analysis was stopped and the corresponding volume of medium containing cells was calculated. Panel E displays the viability assay of analyzed CD34 cells of this measurement. The viable cells appear again in the middle/right position of the forward scatter (FSC) displaying low/no propidium iodide labeling. The few dead cells appear left or in the upper/left position relative to viable cell population. The FACS measurement took an aliqout count of the beads and calculated the number of cells being present within the well, whereas the cytotoxicity, the number of dead cells, was recorded in parallel during this measurement (addition of propidium iodide; final concentration 1 µg/ml). With increasing concentrations of a cytotoxic substance, the number of cell in the dead cell cluster increased significantly (FIG. 2 panel F and G). At the highest inhibitory and cytotoxic concentration very few cells were present anymore in the viable cell cluster and the majority of cells had been killed as evident by increased PI staining or fragmentation (panel H).

A typical example of the calculation of the number of CD34 cells and percentage of dead cells in a well is shown in FIG. 3 for two cytotoxic compounds, namely 5-fluorouracil and doxorubicine. The cell number per well is displayed as bar for each concentration tested. For 5-fluorouracil the cell number decreased significantly between 0.3 and 1.0 µmol/l and at the lowest concentration of 1 ng/ml doxorubicine the cell number was lower already. Applying a $IC_{50}$ calculation program, the $IC_{50}$ values for the inhibitor compounds were calculated to be 0.34 µmol/l and 0.67 ng/ml for 5-fluorouracil and doxorubicine, respectively. The increase of the percentage of dead cells obtained from the analysis of the PI positive cell fraction (FIG. 2 panels E to H) is shown as solid line.

The invention claimed is:

1. Method for simultaneous determination of mammalian cell proliferation inhibition activity and cell toxicity activity of a test substance in a single sample of cells comprising
   a) contacting a proliferating mammalian cell sample that is present in a predetermined amount with said test substance in at least two different predetermined concentrations;
   b) contacting said cell sample with a first fluorescence dye that specifically stains either dead cells or viable cells and optionally with a second fluorescence dye staining all cells;
   c) adding to said cell sample a predetermined amount of latex particles with a size ranging from about 1 to about 20 µm and optionally staining said latex particles with a third fluorescence dye;
   d) determining ratio of the amount of total cells to the amount of latex particles in said cell sample;
   e) determining the ratio of step d) and by flow cytometric analysis in said sample
      the number of dead cells or viable cells to total cells by fluorescence light emitted by said first fluorescence dye at a first wavelength;
      the number of total cells per volume by scatter light at a first angle or alternatively by fluorescence light emitted by said second fluorescence dye at a second wavelength;
      the number of latex particles per volume by scatter light at a second angle or alternatively by fluorescence light emitted by said third fluorescence dye at a third wavelength;
   f) and determining the cell proliferation inhibition activity and toxicity of said test substance by comparing the ratio of viable cells to total cells and the ratio of dead cells to total cells at different concentrations of the test substance.

2. The method of claim 1 wherein the cell sample is present as a cell suspension or as adherent cells.

3. The method of claim 1 wherein the dead cells are stained specifically by a fluorescence dye and the number of latex particles and total cells is measured by differential side scatter light and forward scatter light.

4. The method of claim 3, wherein the cell sample is human $CD34^+$ progenitor cells.

5. The method of claim 1 wherein the cells are cultivated in parallel in multiple devices and the samples are transferred to the flow cytometric analysis apparatus by automated pipetting.

* * * * *